United States Patent [19]
Iwamoto

[11] Patent Number: 5,103,470
[45] Date of Patent: Apr. 7, 1992

[54] CHARACTERISTIC X-RAY DETECTING DEVICE

[75] Inventor: Kanemasa Iwamoto, Ibaraki, Japan

[73] Assignee: Rigaku Industrial Corp., Osaka, Japan

[21] Appl. No.: 562,325

[22] Filed: Aug. 3, 1990

[30] Foreign Application Priority Data

Aug. 3, 1989 [JP] Japan ............................. 1-91014[U]

[51] Int. Cl.$^5$ .................................................. G01T 1/24
[52] U.S. Cl. ......................................... 378/45; 378/44; 250/370.01
[58] Field of Search .................. 250/370.01; 378/44, 378/45, 47, 48, 49

[56] References Cited

U.S. PATENT DOCUMENTS 4,224,517 9/1988 Lubecki et al. ..................... 378/45

FOREIGN PATENT DOCUMENTS 0117307 9/1984 European Pat. Off. .
1042992 9/1966 United Kingdom ................. 378/45

OTHER PUBLICATIONS

Baldin et al., "Use of X-Ray Analyzer with a Semiconductor Detector for Elemental Analysis", *Instrum & Exp. Tech. (USA)* No. 5, Sep.-Oct. 1970, pp. 1475-1477.

Primary Examiner—Janice A. Howell
Assistant Examiner—David P. Porta
Attorney, Agent, or Firm—Birch, Stewart, Kolasch & Birch

[57] ABSTRACT

An X-ray detecting device for detecting characteristic X-rays emitted from a substance to be detected, which device comprises a vessel having a window defined therein for the passage of the characteristic X-rays emitted from the substance, therethrough into the vessel, and an X-ray detector accommodated within the vessel for the detection of the characteristic X-rays entering the vessel through the window. A portion of the vessel positioned on one side closer to the window and away from a sensing surface of the X-ray detector, upon which the characteristic X-rays impinge, and a peripheral lip area of the vessel defining the window have at least a respective area which is exposed to the interior of the vessel. This respective area is formed with a material which does not contain said substance.

20 Claims, 3 Drawing Sheets

CHARACTERISTIC X-RAY DETECTING DEVICE

BACKGROUND OF THE INVENTION

1. Field of the Invention

The present invention relates to a characteristic X-ray detecting device utilizable for the detection of substances in a testpiece.

2. Description of the Prior Art

The characteristic X-ray detecting device is well known as an instrument for detecting substances contained in a testpiece. The detection is generally carried out by exciting the testpiece with radiation and then by analyzing the wavelength of characteristic X-rays (i.e., fluorescent X-rays) emitted from the excited testpiece. The conventional characteristic X-ray detecting device generally comprises a substantially closed vessel having an X-ray incident window defined therein and closed by a lid made of beryllium or the like. The closed vessel contains therein an X-ray detector utilizing, for example, a semiconductor.

With the conventional characteristic X-ray detecting device, a problem has been found in that, when an attempt is made to detect secondary X-rays emitted from a testpiece to be analyzed as a result of excitation of the testpiece with primary X-rays while the detecting device has been positioned close to a surface of the testpiece, one or both of the primary X-rays used for the excitation of the testpiece to be analyzed and of the secondary X-rays (including characteristic X-rays and scattered X-rays) emitted from the testpiece may enter the closed vessel and subsequently impinge upon the inner surface of the closed vessel, resulting in an erroneous measurement induced by X-rays coming from the inner surface excited by the primary or secondary X-rays.

SUMMARY OF THE INVENTION

Therefore, the present invention is intended to substantially eliminate the above discussed problem inherent in the prior art and has for its primary object to provide an improved characteristic X-ray detecting device effective to provide a reliable and accurate measurement of X-rays characteristic of a substance.

To this end, according to the present invention, there is provided an X-ray detecting device for detecting characteristic X-rays emitted from a substance to be detected, which device comprises a vessel having a window defined therein for the passage of the characteristic X-rays emitted from the substance, therethrough into the vessel, and an X-ray detector accommodated within the vessel for the detection of the characteristic X-rays entering the vessel through the window. A portion of the vessel positioned on one side closer to the window and away from a sensing surface of the X-ray detector, upon which the characteristic X-rays impinge, and a peripheral lip area of the vessel defining the window have at least a respective area which is exposed to the interior of the vessel, said respective area being formed with a material which does not contain the substance to be detected.

Preferably, the vessel has a coating of material which does not contain the substance to be detected and wherein the coating is formed on an entire inner surface of the vessel including an annular surface of the peripheral lip area of the vessel defining the window.

Alternatively, the coating may be formed on a portion of an inner surface of the vessel positioned on one side closer to the window and the peripheral lip area of the vessel defining the window.

Again alternatively, the vessel is made of the material which does not contain the substance to be detected.

According to another embodiment of the present invention, the entire inner surface of the vessel may be lined with the coating of the specific material.

In either case, the material for the coating is preferably selected from the group consisting of lead, graphite, and silicon. Where the characteristic X-rays are those emitted from the substance to be detected when the latter is radiated by primary X-rays generated from an X-ray emission source, the material for the coating may be selected from the group consisting of lead, graphite, silicon and a target element used in the X-ray emission source. The target element may be selected from the group consisting of molybdenum, tungsten and chromium.

Preferably, the peripheral lip area of the vessel defining the window is of a shape generally diverging inwardly of the vessel, and the window in the vessel may be closed by a lid made of beryllium.

According to the present invention, even though the primary X-rays used to excite the testpiece to be analyzed or the secondary X-rays emitted from the testpiece impinge upon the inner surface of the vessel and/or the peripheral lip area defining the window in the vessel enough to generate fluorescent X-rays and those fluorescent X-rays are subsequently detected by the X-ray detector, the employment of the coating of the specific material makes it possible that the analysis of the wavelength of the X-rays so detected can result in a separation of the X-rays characteristic of the testpiece from the fluorescent X-rays of the inner surface and/or the peripheral lip area defining the window of the vessel, and, therefore, the accurate and correct measurement of the X-rays characteristic of the testpiece is possible.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined solely by the appended claims. In the accompanying drawings, like reference numerals are used to denote like parts throughout the several views, and:

DETAILED DESCRIPTION OF THE EMBODIMENT

Figure 1:
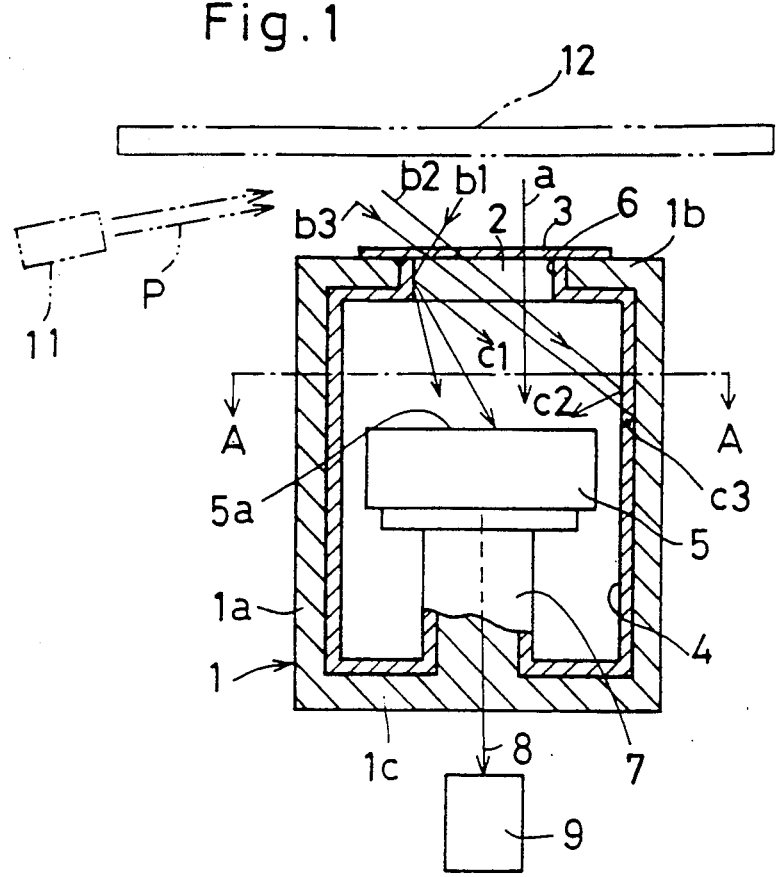
FIG. 1 is a schematic longitudinal sectional view of an X-ray detecting device according to one preferred embodiment of the present invention.
Figure 2:
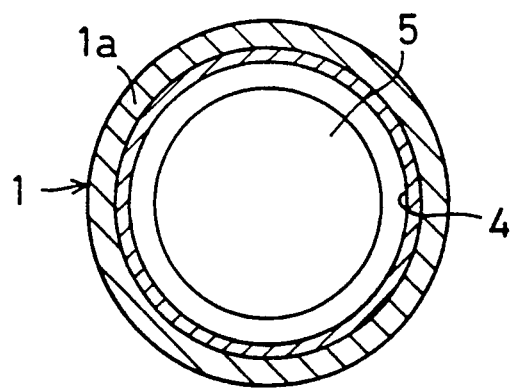
FIG. 2 is a cross-sectional view of the X-ray detecting device taken along the line A—A in FIG. 1.

Referring to the accompanying drawings, FIG. 1 shows a schematic longitudinal sectional view of an X-ray detecting device embodying the present invention and FIG. 2 shows a cross-sectional view of the X-ray detecting device taken along the line A—A in FIG. 1. As shown in FIG. 1, an X-ray analyzing apparatus comprises an X-ray emission source 11 for emitting primary X-rays P towards a testpiece 12 to be analyzed so as to excite the latter, and the X-ray detecting device having a generally cylindrical vessel 1 positioned in the vicinity of the testpiece 12. The cylindrical vessel 1 comprises a generally cylindrical hollow wall 1a having its opposite ends closed by top and bottom end walls 1b and 1c. The top end wall 1b of the cylindrical vessel 1 has a generally round incident window 2 defined therein preferably in coaxial relationship with the center of the top end wall 1b, which window 2 is tightly closed by a lid 3 of, for example, beryllium and fixedly placed on an outer surface of the top end wall 1b of the cylindrical vessel 1.

The cylindrical vessel 1 also comprises a generally cylindrical pedestal 7 integrally formed, or otherwise rigidly connected, with the bottom end wall 1c so as to protrude into the interior of the cylindrical vessel 1 in alignment with the longitudinal axis of the cylindrical vessel 1, and an X-ray detector 5 supported by the cylindrical pedestal 7. The X-ray detector 5 has an X-ray sensing surface 5a for sensing X-rays incident thereupon and may be of any known type, for example, a well-known solid-state X-ray detector utilizing a semiconductor. This X-ray detector 5 is accommodated within the cylindrical vessel 1 and is fixedly mounted on a free end of the cylindrical pedestal 7 with the X-ray sensing surface 5a facing upwards and towards the incident window 2 defined in the top end wall 1b of the cylindrical vessel 1.

The cylindrical vessel 1 is made of, for example, stainless steel which is chosen because of a high resistance to rusting and a relatively high workability, however, the stainless steel contains, in addition to iron and a small quantity of chromium or nickel, some other various metals. In accordance with the present invention, accordingly, the entire inner surface of the cylindrical vessel 1 including an inner surface of the cylindrical hollow wall 1a, an annular inner surface of each of the top and bottom end walls 1b and 1c, an annular surface of a peripheral lip region 6 defining the incident window 2 and a peripheral surface of the cylindrical pedestal 7 is completely covered by a coating 4 made of any known material which is different from and does not contain the substance to be detected, for example, lead.

However, other than the lead, any one of graphite, silicon and a target element such as, for example, molybdenum, tungsten or chromium which is generally used in the X-ray emission source 11 may also be employed as material for the coating 4. These exemplified substances are suited as material for the coating 4 partly because it can easily be formed into a film or a thin layer and partly because of the following reasons.

Lead has a property of absorbing X-rays and is seldom used as a substance to be detected by the X-ray detector 5. With respect to graphite, it contains a carbon element which is not used as a substance to be detected by a standard characteristic X-ray detecting device of a type wherein the beryllium lid 3 is used to close the incident window 2, because C-Kα rays are long in wavelength and are therefore apt to be absorbed by the beryllium lid 3.

In the case where the testpiece 12 to be analyzed is a silicon wafer which is a raw material for a semiconductor product, the substance to be detected from the silicon wafer would be particles of arsenic or stainless steel which form impurities contained in the silicon wafer and silicon itself will not be the substance to be detected. Also, the target element is generally recognized as having a wavelength represented by the primary X-rays P and can therefore be readily distinguished from characteristic X-rays emitted from the testpiece 12.

An output 8 generated from the X-ray detector 5 is supplied to any known wavelength analyzer 9 for the analysis of the wavelength to determine the substance in terms of spectrum of the detected wavelength.

Figure 3:
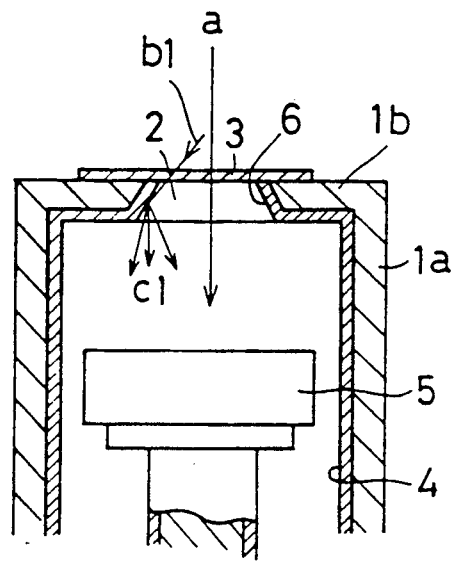
FIG. 3 is a schematic longitudinal sectional view of a portion of the X-ray detecting device according to a second preferred embodiment of the present invention.

While in the foregoing embodiment of the present invention shown in and described with reference to FIGS. 1 and 2 the round incident window 2 defined in the top end wall 1b of the cylindrical vessel 1 has been shown as having a uniform diameter across the thickness of the top end wall 1b, the round incident window 2 may not have a uniform diameter across the thickness of the top end wall 1b and, as shown in FIG. 3, may have a varying diameter across the thickness of the top end wall 1b of the cylindrical vessel 1. Specifically, in the embodiment shown in FIG. 3, the round incident window 2 is of a shape generally diverging inwardly of the cylindrical vessel 1.

As hereinbefore described, most of the characteristic X-rays, indicated by a, generated from the testpiece 12 to be analyzed impinge upon the X-ray detector 5 after having passed through the incident window 2 and, therefore, the analysis of the wavelength of the X-rays detected by the X-ray detector 5 by means of any known method will reveal the composition of the testpiece 12 to be analyzed. Also, portions b1 and b2 of the characteristic X-rays emitted from the testpiece 12 and-/or primary X-rays used to excite the testpiece 12 may pass through the incident window 2 in a direction slantwise relative to the plane occupied by the top end wall 1b and will subsequently impinge upon the peripheral lip region 6 defining the incident window 2 and/or the inner surface of the cylindrical vessel 1 thereby to emit fluorescent X-rays C1 and C2, respectively. Detection of the fluorescent X-rays C1 and C2 would result in an erroneous measurement.

However, according to the present invention, since the entire inner surface of the cylindrical vessel 1 including the annular surface of the peripheral lip region 6 is covered by the coating 4 of the known material such as, for example, lead, different from the substance to be detected, the fluorescent X-rays C1 and C2 even though detected by the X-ray detector 5 can readily and easily be separated from the characteristic X-rays by the wavelength analysis performed by the wavelength analyzer 9. On the other hand, fluorescent X-rays C3 generated by X-rays b3 having passed through the coating 4 and tending to be reflected by the inner surface of the cylindrical hollow wall 1a towards the X-ray detector 5 are attenuated by absorption into the lead coating 4 and will not therefore affect the result of measurement, thus making it possible to accomplish an accurate and reliable analysis.

Where the incident window 2 is of a shape generally diverging in a direction inwardly of the cylindrical vessel 1 according to the second preferred embodiment of the present invention shown in FIG. 3, the possibility can be advantageously minimized that the X-rays b1 may impinge upon that portion of the coating 4 which covers the annular surface of the peripheral lip region 6 and that the fluorescent X-rays C1 generated as a result of the impingement of the X-rays b1 may impinge upon the X-ray detector 5.

Figure 4:
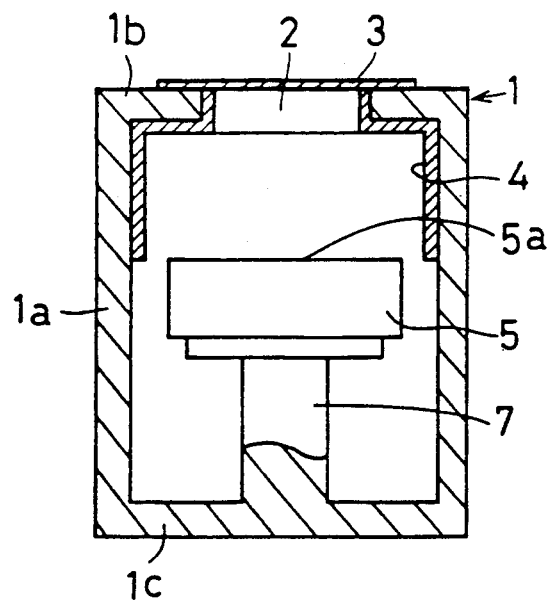
FIG. 4 is a schematic longitudinal sectional view of the X-ray detecting device according to a third preferred embodiment of the present invention.

While in any one of the foregoing preferred embodiments of the present invention the entire inner surface of the cylindrical vessel 1 has been shown and described as lined with the coating 4, the coating 4 may not be always made on the entire inner surface of the cylindrical vessel 1 and may be made on an upper portion of the inner surface of the cylindrical vessel 1 as shown in FIG. 4. Specifically, according to a third preferred embodiment of the present invention shown in FIG. 4, only that upper portion of the inner surface of the cylindrical vessel 1 adjacent the incident window 2 and above the level flush with the X-ray sensing surface 5a of the X-ray detector 5 is lined with the coating 4. That upper portion of the inner surface of the cylindrical vessel 1 is formed by the annular surface of the peripheral lip region 6 defining the incident window 2, and a portion positioned on one side away from the sensing surface 5a and closer to the window 2.

Figure 5:
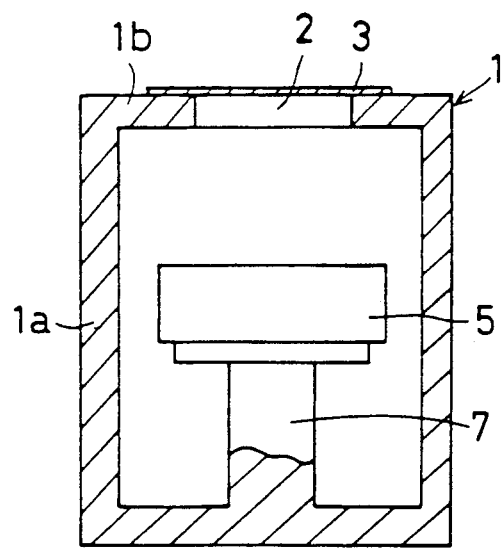
FIG. 5 is a schematic longitudinal sectional view of the vessel according to a fourth preferred embodiment of the present invention.

In addition, unlike any one of the first to third preferred embodiments of the present invention, the vessel 1 in its entirety may be made of material different from, and which does not contain, the substance to be detected. In other words, the vessel 1 may be made of the same material as that for the coating 4. This is illustrated in FIG. 5 as a fourth preferred embodiment of the present invention.

Figure 6:
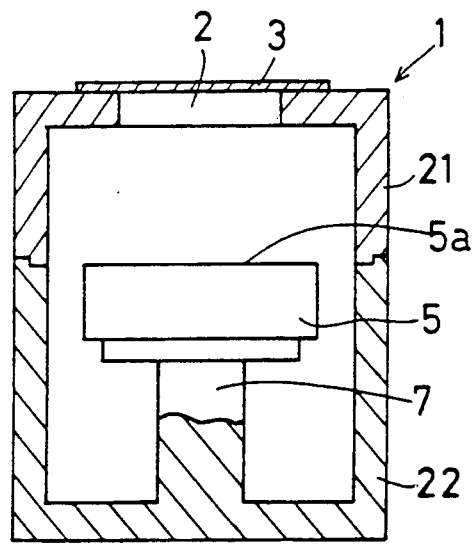
FIG. 6 is a view similar to FIG. 5, showing the vessel according to a fifth preferred embodiment of the present invention.

Moreover, as shown in FIG. 6, the vessel 1 may be of two component type comprising a lower body 22 having the bottom and an upper body 21 having the window 2 defined therein, the upper body 21 being mounted over the lower body 22 with a seamless joint formed by the use of any suitable bonding means such as, for example, a soldering technique. While the lower body 22 may be made of the same material as used for the vessel 1 according to any one of the first to third preferred embodiments of the present invention, for example, stainless steel, the upper body 22 should be made of material different from and which does not contain the substance to be detected. The boundary between the upper and lower vessel bodies 21 and 22 is preferably selected to correspond to or in flush with the sensing surface 5a of the X-ray detector 5 positioned inside the vessel 1.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. For example, the cross-sectional shape of the vessel 1, that of the pedestal 7 and/or the shape of the incident window 2 may not be always limited to that shown in and described with reference to the accompanying drawings. Accordingly, such changes and modifications are, unless they depart from the spirit and scope of the present invention as delivered from the claims annexed hereto, to be construed as included therein.

What is claimed is:

1. An X-ray detecting device for detecting characteristic X-rays emitted from the substance of a testpiece to be detected, which comprises:
    a vessel, said vessel having a wall with a non-collimator window defined therein for the passage of the characteristic X-rays emitted from the substance, therethrough into said vessel, said wall being located closely adjacent to and in spaced apart relationship from the testpiece; and
    an X-ray detector, said X-ray detector having a sensing surface and being within said vessel for the detection of the characteristic X-rays entering said vessel through said window;
    wherein a portion of said vessel positioned on one side closer to said window and away from said sensing surface upon which the characteristic X-rays impinge, including a peripheral lip area of said vessel defining said window have at least a surface area which is exposed to said interior of the vessel, said surface area being formed with a material which does not contain the substance to be detected.

2. The X-ray detecting device as claimed in claim 1, wherein said vessel has a coating of material which does not contain the substance to be detected and wherein said coating is formed on an entire inner surface of said vessel including an annular surface of said peripheral lip area of said vessel defining said window.

3. The X-ray detecting device as claimed in claim 1, wherein said vessel has a coating of material which does not contain the substance to be detected and wherein said coating is formed on a portion of an inner surface of said vessel positioned on one side closer to said window and the peripheral lip area of said vessel defining said window.

4. The X-ray detecting device as claimed in claim 1, wherein said vessel is made of said material which does not contain the substance to be detected.

5. The X-ray detecting device as claimed in claim 1, wherein said portion of the vessel positioned on one side closer to said window including said peripheral lip area of said vessel defining said window are formed of said material which does not contain the substance to be detected.

6. The X-ray detecting device as claimed in claim 1, wherein the characteristic X-rays are generated from a testpiece when the testpiece is radiated by primary X-rays generated from an X-ray emission source.

7. The X-ray detecting device as claimed in claim 1, further comprising a lid made of beryllium, said window being closed by said lid.

8. The X-ray detecting device as claimed in claim 1, wherein said peripheral lip area defining said window is of a shape generally diverging in a direction inwardly of said vessel.

9. The X-ray detecting device as claimed in claim 1, wherein said material which does not contain the substance to be detected is selected from the group consisting of lead, graphite and silicon.

10. The X-ray detecting device as claimed in claim 6, wherein said material which does not contain the substance to be detected is selected from the group consisting of lead, graphite, silicon and a target element used in said X-ray emission source. .

11. The X-ray detecting device as claimed in claim 10, wherein said target element is selected from the group consisting of molybdenum, tungsten and chromium.

12. An X-ray detecting device for detecting characteristic X-rays emitted from the substance of a testpiece to be detected, comprising:

a vessel, said vessel including a cylindrical wall structure, a first end wall, the first end wall including a window defined therein for the passage of the characteristic X-rays emitted from the substance, therethrough into said vessel, said window having a peripheral lip area, a second end wall and a cylindrical pedestal, said pedestal having a peripheral surface, being connected to said second end wall, and extending toward said window from said second end wall, said second end wall having an annular inner surface surrounding and extending radially outward from said pedestal;

an X-ray detector accommodated within the vessel, said X-ray detector having a sensing surface upon which the characteristic X-rays impinge for the detection of the characteristic X-rays entering said vessel through said window, the X-ray detector being supported by said pedestal with said sensing surface facing said window in spaced apart relation therefrom;

wherein said cylindrical wall structure includes a first portion, said first portion extending from adjacent the level of said sensing surface to said first end wall, and a second portion, said second portion extending from adjacent the level of said sensing surface to said second end wall;

and wherein a first inner surface area is formed by said first portion, said first end wall and said peripheral lip area, and a second inner surface area is formed by said second portion, said annular inner surface, and said peripheral surface.

13. The X-ray detecting device as claimed in claim 12, wherein said vessel further includes a coating of a material which does not contain the substance to be detected, said coating being formed on said first and second inner surface area.

14. The X-ray detecting device as claimed in claim 12, wherein said vessel further includes a coating of a material which does not contain the substance to be detected, said coating being formed on said first inner surface area.

15. The X-ray detecting device as claimed in claim 12, wherein said first and second portions, said first and second end walls and said pedestal are made of a material which does not contain the substance to be detected.

16. The X-ray detecting device as claimed in claim 12, wherein said first portion and said first end wall are formed of a material which does not contain the substance to be detected.

17. The X-ray detecting device as claimed in claim 13, wherein the peripheral lip area is of a shape generally diverging in a direction inwardly of said vessel.

18. The X-ray detecting device as claimed in any of claims 12, 13, 14, 15, 16 or 17, wherein said material which does not contain the substance to be detected is selected from the group consisting of lead, graphite, silicon and a target element used in an X-ray emission source.

19. The X-ray detecting device as claimed in claim 18, wherein the target element is selected from the group consisting of molybdenum, tungsten and chromium.

20. The X-ray detecting device as claimed in claim 19, wherein the characteristic X-rays are generated from a testpiece when the testpiece is radiated by primary X-rays generated from an X-ray emission source.

* * * * *